(12) United States Patent
Häussermann et al.

(10) Patent No.: US 11,951,224 B2
(45) Date of Patent: Apr. 9, 2024

(54) DISINFECTION DEVICE

(71) Applicant: Dürr Systems AG, Bietigheim-Bissingen (DE)

(72) Inventors: Patrick Häussermann, Korb (DE); Bernhard Seiz, Lauffen (DE); Kevin Preuss, Mühlacker (DE); Harry Krumma, Bönnigheim (DE); Michael Baumann, Flein (DE); Mark E. Dion, St. Clair Shores, MI (US)

(73) Assignee: Dürr Systems AG, Bietigheim-Bissingen (DE)

( * ) Notice: Subject to any disclaimer, the term of this patent is extended or adjusted under 35 U.S.C. 154(b) by 659 days.

(21) Appl. No.: 16/973,797

(22) PCT Filed: Jun. 5, 2019

(86) PCT No.: PCT/EP2019/064683
§ 371 (c)(1),
(2) Date: Dec. 10, 2020

(87) PCT Pub. No.: WO2019/238503
PCT Pub. Date: Dec. 19, 2019

(65) Prior Publication Data
US 2021/0260233 A1    Aug. 26, 2021

(30) Foreign Application Priority Data
Jun. 13, 2018   (DE) .................... 10 2018 114 179.3

(51) Int. Cl.
*A61L 2/22* (2006.01)
*A61L 2/26* (2006.01)
(Continued)

(52) U.S. Cl.
CPC ................. *A61L 2/22* (2013.01); *A61L 2/26* (2013.01); *B05B 3/1014* (2013.01); *B05B 3/105* (2013.01);
(Continued)

(58) Field of Classification Search
None
See application file for complete search history.

(56) References Cited

U.S. PATENT DOCUMENTS 3,192,167 A    6/1965  Ogawa et al.
10,188,764 B2  1/2019  Cunningham
(Continued)

FOREIGN PATENT DOCUMENTS

CN      204395212 U    6/2015
DE    102004050400 A1   4/2006
(Continued)

OTHER PUBLICATIONS

EP2441523A1—translated document (Year: 2012).*
(Continued)

*Primary Examiner* — Jelitza M Perez
(74) *Attorney, Agent, or Firm* — Bejin Bieneman PLC

(57) ABSTRACT

The disclosure relates in particular to an apparatus for disinfecting at least one room, in particular for one or more persons, preferably a dwelling space or treatment room, for example a treatment room in a building, in particular a sickroom, a patient room and/or an operating theatre, by means of an atomiser. Specifically, the apparatus is characterised in that the atomiser includes a rotatable bell cup for atomising a disinfectant into the room. The disclosure relates to an associated method and furthermore to the use of a bell cup for atomising a disinfectant in a room for, in particular, one or more persons.

12 Claims, 10 Drawing Sheets

(51) Int. Cl.
  *B05B 3/10* (2006.01)
  *B05B 7/00* (2006.01)
  *B05B 12/00* (2018.01)
  *B05B 14/00* (2018.01)
  *B05B 15/55* (2018.01)

(52) U.S. Cl.
  CPC .......... *B05B 7/0075* (2013.01); *B05B 12/006* (2013.01); *B05B 14/00* (2018.02); *B05B 15/55* (2018.02); *A61L 2202/14* (2013.01); *A61L 2202/15* (2013.01); *A61L 2202/17* (2013.01); *A61L 2202/25* (2013.01)

(56) References Cited

U.S. PATENT DOCUMENTS

| | | |
|---|---|---|
| 2014/0119992 A1 | 5/2014 | Cunningham |
| 2015/0140235 A1 | 5/2015 | Meier et al. |

FOREIGN PATENT DOCUMENTS

| | | | |
|---|---|---|---|
| DE | 102008037035 A1 | 2/2010 | |
| DE | 102009037604 A1 | 2/2011 | |
| DE | 102010022309 A1 | 12/2011 | |
| EP | 2441523 A1 | 4/2012 | |
| EP | 2441523 A1 * | 4/2012 | .......... A01M 7/0014 |
| FR | 1310867 A * | 11/1962 | |
| FR | 1310867 A | 11/1962 | |
| FR | 2555452 A1 | 5/1985 | |
| FR | 2886559 A1 | 12/2006 | |
| JP | H08257453 A | 10/1996 | |
| JP | H11226454 A | 8/1999 | |
| JP | 2000316956 A | 11/2000 | |
| JP | 3136927 U | 11/2007 | |
| JP | 2013039506 A | 2/2013 | |
| JP | 2014161701 A | 9/2014 | |
| KR | 20-0436417 Y1 | 8/2007 | |
| WO | 2004030828 A1 | 4/2004 | |
| WO | 2009040684 A1 | 4/2009 | |
| WO | 2012060153 A1 | 5/2012 | |
| WO | 2017002769 A1 | 1/2017 | |

OTHER PUBLICATIONS

FR1310867A—translated document (Year: 1962).*
Ballu, P. (EP2441523A1)—translated document (Year: 2012).*
Chinese Office Action dated Mar. 1, 2023 for related application No. CN201980039497.9 (14 pages; with English machine translation).
International Search Report and Written Opinion for PCT/EP2019/064683 dated Nov. 27, 2019 (21 pages; with English machine translation).
German Patent and Trademark Office—Office Action for DE102018114179.3 dated Jun. 18, 2019 (3 pages; English translation not available).
Notification of Reasons for Rejection from JPO in related application No. JP2020569035 dated Jun. 20, 2023 (28 pages; with English machine translation).
Korean Intellectual Property Office Notice of Preliminary Rejection for related application No. KR10-2020-7035854 dated Jun. 30, 2023 (26 pages; with English translation).

* cited by examiner

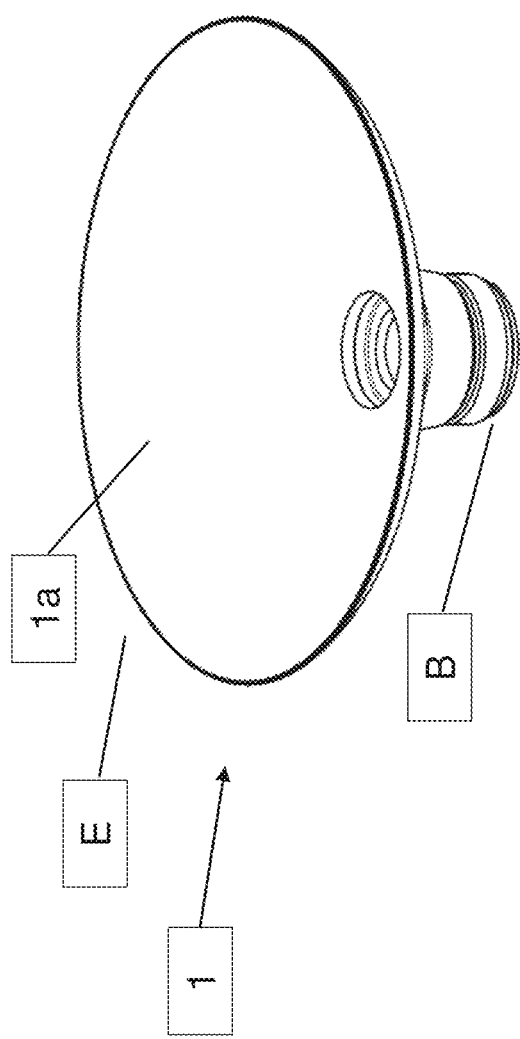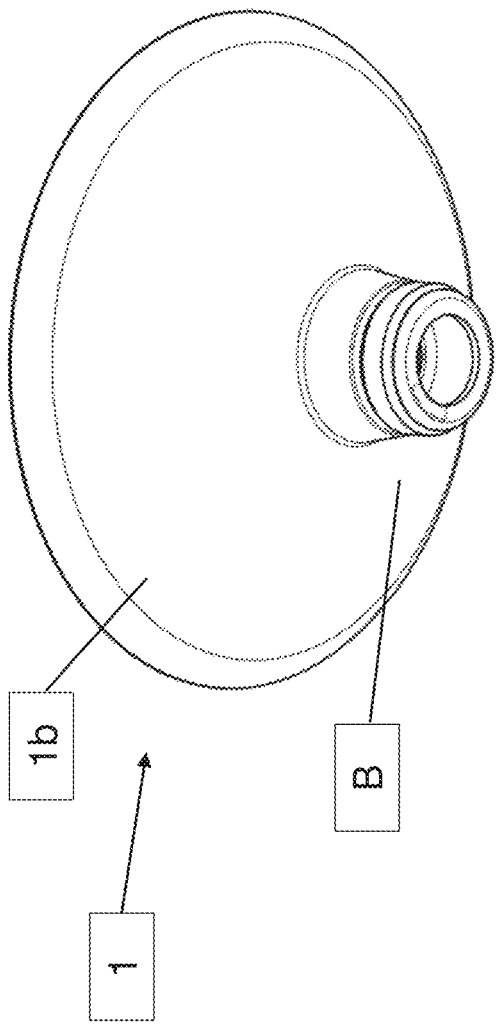

DISINFECTION DEVICE

CROSS-REFERENCE TO RELATED APPLICATIONS

This application is a national stage of, and claims priority to, Patent Cooperation Treaty Application No. PCT/EP2019/064683, filed on Jun. 5, 2019, which application claims priority to German Application No. DE 10 2018 114 179.3, filed on Jun. 13, 2018, which applications are hereby incorporated herein by reference in their entireties.

FIELD

The disclosure relates in particular to an apparatus for disinfecting at least one room, preferably for one or more persons, for example a dwelling space, storage room, cold storage room and/or treatment room, for example a treatment room in a building, in particular a sickroom, a patient room and/or an operating theatre, by means of an atomiser suitable for atomising a disinfectant into the room.

BACKGROUND

It is known to disinfect rooms such as sickrooms or operating theatres in hospitals or doctors' surgeries on a regular basis, in particular to eliminate bacteria, viruses, fungi, etc. US 2014/0119992 A1 and U.S. Pat. No. 10,188,764 describes for this a process in which a disc, a nozzle or a piezoelectric ultrasonic atomiser generates a disinfectant mist.

BRIEF DESCRIPTION OF THE DRAWINGS

FIG. 10 shows a perspective view from above of a bell cup according to an embodiment of the disclosure, and FIG. 11 shows a perspective view from below of the bell cup of FIG. 10.

DETAILED DESCRIPTION

Figure 1:
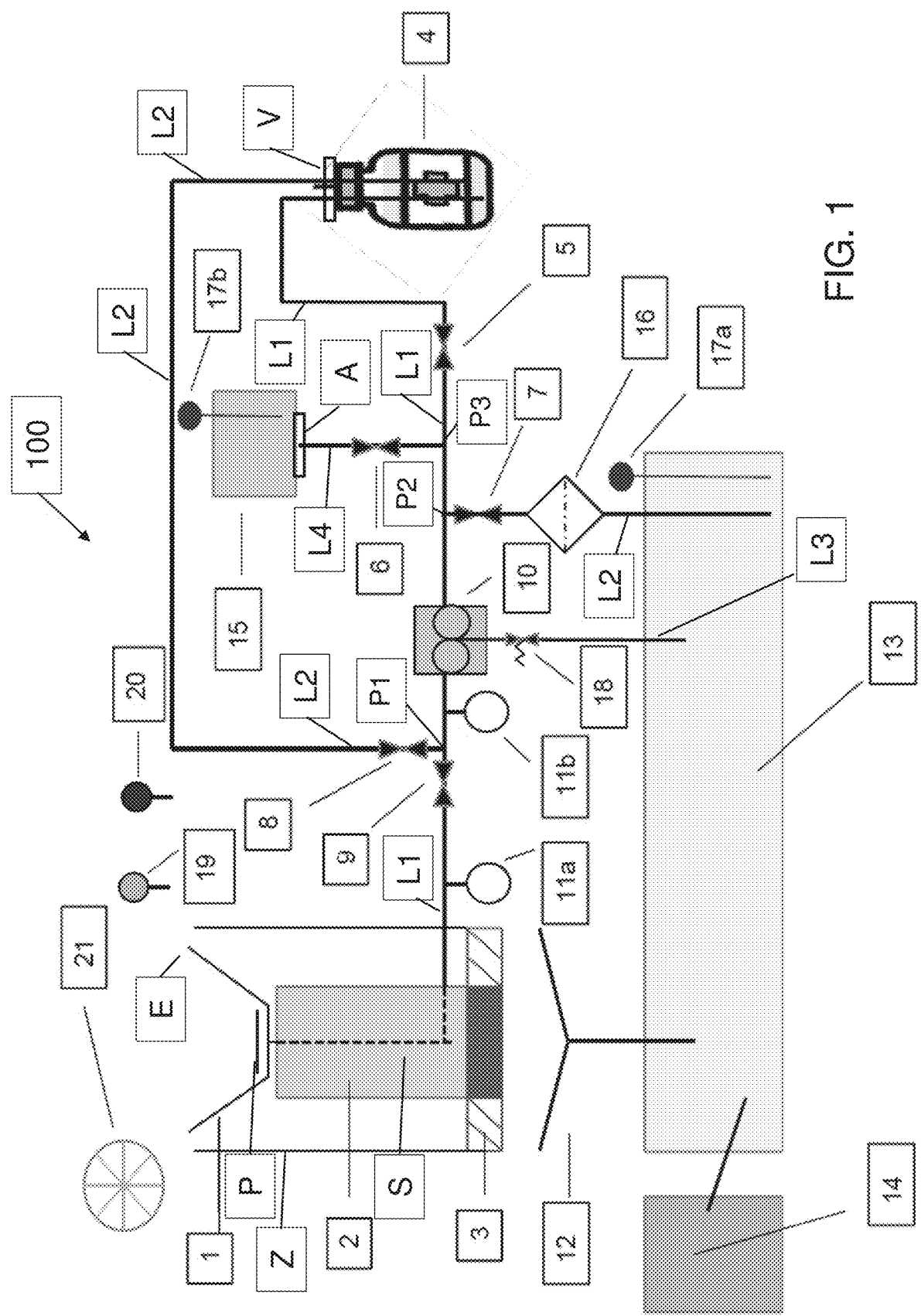
FIG. 1 shows a schematic view of an apparatus according to an embodiment of the disclosure.

A task of the disclosure is to provide an apparatus for disinfecting at least one room, preferably accessible by one or more persons, with improved performance and/or improved atomising properties.

The disclosure relates to an apparatus for disinfecting at least one room, for example a room for one or more persons, preferably a dwelling space, storage room, cold storage room and/or treatment room (suitable for humans or animals), for example a treatment room in a building, in particular a sickroom, a patient room and/or an operating theatre, for example in a hospital or doctor's surgery. However, the dwelling space may also include, for example, classrooms, bathrooms, toilets, sanitary facilities or compartments of aircraft, ships or other vehicles. The dwelling space may preferably also include a veterinary dwelling space and/or waiting room.

The apparatus includes a suitable atomiser, preferably a rotatable bell cup (in particular a so-called high rotation bell) for atomising a disinfectant into the room. The bell cup is preferably essentially funnel-shaped, but can also be essentially disc-shaped or otherwise.

The disclosure is based, inter alia, on the principle of using a rotatable bell cup to atomise disinfectant into the room. Bell cups and their mode of operation are known from the technical field of painting motor vehicle bodies by means of rotary atomisers. At this, the bell cup serves to atomise the paint through centrifugal force and discharge it onto the vehicle body in the form of a paint spray jet in order to produce a paint path. Surprisingly, it has been discovered that bell cups are also suitable for atomising disinfectant and at this, in particular, exhibit very good atomising performance and/or very good atomising properties.

The apparatus may have an electric motor and/or a turbine, for example a pneumatically driven turbine, in particular an air turbine, to drive the bell cup, preferably via a hollow drive shaft.

The apparatus may, for example, have at least one blower (for example a fan), the blower serving to transport and distribute disinfectant atomised by means of the bell cup. A blower may be arranged, for example, to distribute the disinfectant essentially upwards. A blower may be arranged, for example, to distribute the disinfectant out to the sides. One of these blowers can also be used to cool the electric motor and/or the air turbine.

At least sections of the bell cup, the electric motor, the air turbine and/or a blower may be accommodated in an atomiser housing.

The apparatus may, for example, have a disinfectant line connectable to the bell cup to supply disinfectant to the bell cup.

The apparatus may have a suitably detachable or non-detachable connecting device for connection to a container for holding the disinfectant and the connecting device may be connected to the bell cup via the disinfectant line, in particular to supply disinfectant to the bell cup.

The apparatus can preferably have at least one suitable electrically, hydraulically or pneumatically operated delivery device for conveying and/or dosing disinfectant for the disinfection process.

The apparatus may have at least one flow measuring device (for example one or more sensors) for the preferably contactless measurement of a volume flow preferably of the disinfectant and/or a rinsing agent.

A flow measuring device may, for example, be disposed between the bell cup and a bell cup valve (atomiser valve) disposed downstream of the delivery device, wherein alternatively or in addition a flow measuring device may, for example, be disposed between the delivery device and a bell cup valve disposed downstream of the delivery device.

The apparatus may, for example, have a receiving container for receiving and preferably recovering any liquid lost in the disinfection process (for example disinfectant not dispensed, rinsing agent, deposited moisture, etc.).

The receiving container may preferably serve to receive liquid deposited from the disinfectant on or in the atomiser housing, whereby, for example, the deposited liquid can be fed to the receiving container, especially via a funnel.

The apparatus may, for example, have at least one air dehumidifier to dehumidify air in the room, for example with a total dehumidification capacity of, for example, over 600 or over 700 cubic metres per hour.

The at least one air dehumidifier may preferably be connected to the receiving container in order to supply the receiving container with moisture (liquid) extracted from the air.

The delivery device may be connected to the receiving container via a line in order to supply liquid, for example rinsing agent and/or disinfectant, to the receiving container via the line, especially if there is excess pressure at a pressure relief valve. The pressure relief valve may, for example, be disposed in the line between the delivery device and the receiving container or in the disinfectant line downstream of the delivery device or on or in the delivery device. The line may, for example, be connected directly to the delivery device.

The apparatus may have a lost-liquid line and, for example, the receiving container can be emptied via the lost-liquid line and/or can be connected to the connecting device.

Lost liquid may be fed from the receiving container via the connecting device to the disinfectant container previously emptied during the disinfection process for disposal.

On its way from the receiving container to the connecting device, the lost liquid may preferably pass at least one of the following: a filter device for filtering the lost liquid, the delivery device, a receiving container valve which is preferably disposed downstream of the filter device and/or upstream of the delivery device, a lost-liquid return valve, which is preferably disposed downstream of the delivery device and/or upstream of the connecting device, and/or a flow measuring device for measuring a volume flow, preferably of the disinfectant and/or a rinsing agent.

The apparatus may, for example, have a suitably detachable or non-detachable rinsing agent connection for connection to a rinsing agent container for receiving a rinsing agent in order to rinse, while in a rinsing mode, at least sections of the disinfectant line and/or the lost-liquid line with rinsing agent.

The rinsing agent connection can be connected to the disinfectant line, for example via a rinsing agent line, the rinsing agent line preferably including a rinsing agent valve before leading into the disinfectant line.

The apparatus may be operable for the disinfection process in a disinfection mode in order to disinfect the room.

The apparatus may be operable in a recovery mode in order to recover liquid lost due to the disinfection process and/or is operable in a rinsing mode in order to rinse at least sections of the disinfectant line and/or the lost-liquid line.

The delivery device can be used, for example, in recovery mode to convey lost liquid from the receiving container and/or in rinsing mode to convey rinsing agent from the rinsing agent container, and during the disinfection process to feed disinfectant to the bell cup.

The lost-liquid line can be connected to the disinfectant line at two junction points.

A junction point is preferably disposed between the delivery device and a bell cup valve which is suitably disposed in the disinfectant line downstream of the delivery device. Alternatively, or in addition, a junction point is disposed between the delivery device and a disinfectant valve disposed in the disinfectant line suitably upstream of the delivery device.

The rinsing agent line can be connected to the disinfectant line at a junction point. The junction point is preferably disposed between the delivery device and a disinfectant valve disposed in the disinfectant line upstream of the delivery device.

The apparatus may have a multi-functional container for holding disinfectant for the disinfection process and for example also for holding rinsing agent for the rinsing mode, so that preferably the multi-functional container can be filled and operated suitably successively with disinfectant for the disinfection process and/or with rinsing agent while in a rinsing mode.

The multi-functional container is, for example, integrable into the disinfectant line and/or the rinsing agent line.

The multi-functional container may be connectable to the connecting device, preferably via the disinfectant valve, and/or connectable to the rinsing agent connection, preferably via the rinsing agent valve.

The bell cup may be connected to a hollow drive shaft to drive the bell cup. The hollow drive shaft is preferably driven by the electric motor and/or the air turbine.

A supply line in the hollow drive shaft is preferably part of the disinfectant line.

Disinfectant can be supplied to the bell cup preferably through the hollow drive shaft.

The supply line in the hollow drive shaft may in particular include a disinfectant outlet nozzle, for example mounted thereon, the disinfectant outlet nozzle preferably being accommodated in a base of the bell cup and/or having a reduced passage cross-section for the disinfectant in comparison with the passage cross-section of the hollow drive shaft.

The bell cup can work in conjunction with a cup suitably co-rotatable with the bell cup, the disinfectant being distributed to the bell cup by means of the cup.

The cup is preferably mounted on the bell cup.

The bell cup is preferably mounted on the hollow drive shaft.

The bell cup and the cup preferably functions essentially as follows: The disinfectant emerging from the supply line in the hollow drive shaft, in particular from the disinfectant outlet nozzle, meets the rotating cup and is thereby distributed through centrifugal force onto an inner face of the rotating bell cup, from where the disinfectant is led to a bell cup spray edge for spraying and atomisation.

The cup is preferably an essentially disc-shaped deflector and/or distributor cup.

The cup is preferably arranged coaxially with the bell cup and/or the hollow drive shaft.

The cup is preferably rotationally fixed to the bell cup.

The cup may be disposed, for example, at an axial distance of between approx. 0.05 mm to approx. 5 mm, typically between 0.75 mm and 2 mm, from an outlet orifice of the hollow drive shaft, in particular from the disinfectant outlet nozzle.

It is possible for the disinfectant to pass at least one of the following on its way to the bell cup: a disinfectant valve suitably upstream of the delivery device, a bell cup valve suitably downstream of the delivery device, the delivery device, the electric motor or the air turbine, the hollow drive shaft (in particular its supply line) for example with disinfectant outlet nozzle, the plate, and/or at least one flow measuring device for measuring a volume flow, in particular of disinfectant and/or rinsing agent volume flow.

The delivery device may, for example, comprise at least one pump and/or at least one piston system, suitably driven by electrical, pneumatic or hydraulic means.

It is possible for the rinsing agent to pass at least one of the following in rinsing mode: the rinsing agent valve, the delivery device, a section of the disinfectant line, the hollow drive shaft, a section of the lost-liquid line, at least one flow measuring device, the bell cup valve suitably disposed in the disinfectant line downstream of the delivery device, the electric motor or air turbine, the bell cup, the cup, the lost-liquid return valve suitably disposed in the lost-liquid line downstream of the delivery device, and/or the connecting device.

The delivery device and especially the pump may be used to deliver at least one of the following: the disinfectant from the disinfectant tank, the rinsing agent from the rinsing agent tank, and/or the lost liquid from the receiving container.

The piston system may for example comprise at least one of the following: a disinfectant piston system, the disinfectant container being preferably integrable into the disinfectant piston system, a rinsing agent piston system, the rinsing agent container being preferably integrable into the rinsing agent piston system, and/or a disinfectant-rinsing agent piston system, the multi-functional container being preferably integrable into the disinfectant-rinsing agent piston system.

The apparatus may have at least one blower suitably arranged upstream of the bell cup for transporting and distributing disinfectant atomised by means of the bell cup, and/or at least one blower suitably arranged downstream of the bell cup for transporting and distributing disinfectant atomised by means of the bell cup.

The blower suitably disposed upstream of the bell cup may be arranged coaxially with the bell cup, for example in order to distribute disinfectant upwards to a ceiling of the room and/or to cool the electric motor or the air turbine.

The blower suitably disposed downstream of the bell cup is preferably arranged non-coaxially with the bell cup and/or laterally adjacent to the bell cup, for example in order to distribute disinfectant sideways, for example to one or more walls of the room.

The apparatus may have a humidity measuring device (for example one or more sensors), for example with a regulating effect and/or controlling effect on a disinfection process of the apparatus, the humidity measuring device serving in particular to measure a humidity in the room. The regulating effect may, for example, be designed with or without feedback.

The apparatus may have a temperature measuring device (for example one or more sensors), for example with a regulating and/or controlling effect on a disinfection process of the apparatus, the temperature measuring device serving in particular to measure temperature in the at least one room. The regulating effect may, for example, be designed with or without feedback.

The apparatus may for example have at least one level measuring device (for example one or more sensors) for measuring a fill level in the disinfectant container, for measuring a fill level in the receiving container and/or for measuring a fill level in the rinsing agent container. The level measuring device can measure the fill level for example via the weight of the respective container and thus preferably based on gravity, or, for example, via level sensors. The process can only be enabled for example if the fill level is satisfactory.

It is possible for the disinfectant container, the rinsing agent container and/or the multi-functional container to be designed as a replaceable single-use container or as a, for example, refillable container permanently integrated into the apparatus, suitably in the form of a refillable tank.

It is possible for the bell cup to have a speed of between a minimum of 30,000 and, for example, a maximum of 70,000 revolutions per minute during operation.

The bell cup and consequently the apparatus may for example have an atomising capacity of at least 50, 100, 150 or 200 millilitres per minute and/or a circulating air volume of at least 1.5, 10 or 15 cubic metres per minute.

The bell cup preferably has an essentially annular bell cup spray edge for spraying disinfectant, the disinfectant being suitably atomised at the bell cup spray edge. The bell cup spray edge can, for example, have a diameter between 40 mm and 120 mm.

The apparatus may have at least one space measuring device (e.g. one or more sensors) for measuring the space, a disinfection process of the apparatus taking place depending on measurement data from the space measuring device, or the disinfection process of the apparatus being prevented from starting for example if it is detected that the apparatus is improperly positioned in the space or the space appears unsuitable for a disinfection process.

The apparatus may, for example, have a gas directing ring, preferably with one or more leakage openings. The gas directing ring may preferably have the task of conducting a gas (particularly air) on the outer face (e.g. of the bell cup). The gas may, for example, meet the disinfectant dispensed by the bell cup, in particular so as to convert the disinfectant into the required form and/or reduce its droplet size.

The gas directing ring is preferably arranged so that the gas meets the disinfectant dispensed by the bell cup spray edge via an outer face of the bell cup.

The gas directing ring can have a large number of leakage openings disposed in a ring.

The gas directing ring may, for example, suitably encase a base of the bell cup (for example a mounting section) and/or part of an outer face of the bell cup in an essentially annular configuration.

The apparatus may comprise at least one detection device (e.g. one or more sensors, detection by means of RFID [radio-frequency identification] or bar code, etc.) for detecting the disinfectant (e.g. type, composition, etc.), for detecting the rinsing agent (e.g. type, composition, etc.) and/or for detecting a rotation speed of the bell cup (for example, rotation speed too slow or even a non-rotatable bell cup, or rotation speed too fast). In the context of the invention, detection of the rotation speed of the bell cup may also include, for example, detection of the rotation speed of the hollow drive shaft, the electric motor or the air turbine or the derivation of other suitable characteristic values. Detection can thus be direct or indirect as suitable in the context of the invention.

Operation of the apparatus can be interrupted or prevented (for example, does not start) if the detection device detects an unsuitable disinfectant, an unsuitable rinsing agent and/or an unsuitable speed. For example, a supply of disinfectant can be interrupted or prevented, in particular if the bell cup does not rotate or does not rotate at a predefined speed and/or an incorrect disinfectant is detected.

The atomised disinfectant can have droplets with a size, in particular a diameter, of between essentially 1 µm and 50 µm, preferably between 3 µm and 10 µm.

It is possible, for example, to achieve the following drop distribution (volumetric/numerical range):

Numerical distribution DN(50)=preferably 0.1 µm to 10 µm

Volumetric distribution DV(50)=preferably 5 µm to 50 µm

Droplet distribution is suitably measured with the Malvern Instruments measuring system over 1000 measuring points per second at a distance of 300 mm over a range of 100 mm from the atomiser, in particular the bell cup.

The apparatus may have a for example portable control unit (e.g. tablet, app, etc.), which allows the device to be controlled via a wired or wireless connection (e.g. Wi-Fi, Bluetooth, etc.).

The disclosure also includes a mobile transport housing with an apparatus as disclosed herein. The mobile transport housing is used to transport the apparatus so that the apparatus can be transported to different rooms.

The transport housing is able to expose the bell cup at least partially in order to atomise disinfectant, and/or the receiving container is positioned below the level of the bell cup and/or the at least one blower, so that lost liquid can be led to the receiving container by gravity.

The transport housing can be provided with sound-absorbing material, for example.

The transport housing may preferably be part of a trolley, equipped with castors, for example.

The transport housing may, for example, include a sealing cup, whereby the sealing cup divides an inner space of the transport housing into a dry section and a wet section.

The disclosure further includes a method for disinfecting at least one room, for example a room for one or more persons, preferably with an apparatus as disclosed herein, wherein a rotating bell cup atomises a disinfectant into the room. The bell cup can be designed as disclosed herein.

The disclosure also includes the use of a bell cup for atomising a disinfectant for disinfecting at least one room, for example a room for one or more persons. The bell cup can be designed as disclosed herein.

It should be noted that the device is usually placed in a room by an operator so that the device can carry out the disinfection process there. However, it is expedient that no person should be in the room during the disinfection process.

It should also be noted that the containers mentioned herein, particularly the disinfectant container and/or the rinsing agent container, may be designed as single-use container or as a refillable tank for repeated use. Preferably, therefore, the connecting device and/or the rinsing agent connection may suitably be a non-detachable connection, to a tank for example, or a detachable connection, to a single-use container for example. The non-detachable connection can be, for example, a one-piece integral connection, a glued connection or a welded connection, etc. between the container/tank and the line, especially the disinfectant line or the rinsing agent line.

It should further be noted that the apparatus preferably includes a bell cup. However, the disclosure also embraces designs with a different atomiser variant, so that the bell cup is optional and can be replaced by a different atomising element.

The rinsing agent valve, the receiving container valve, the lost-liquid return valve and/or the bell cup valve is preferably controllable, for example electrically, pneumatically, magnetically or hydraulically.

The annular bell cup spray edge may, for example, have a diameter of between 65 mm and 120 mm, preferably 80 mm+/−10 mm, whereby alternatively or additionally an internal angle alpha of an inner face of the bell cup may be for example between 5° and 45°, preferably 30°+/−5°.

An external angle beta of the outer face of the bell cup can be between 1° and 80°, preferably 30°+/−5°.

The internal angle alpha is preferably smaller than the external angle beta.

The inner face of the bell cup may have a peripheral zone, in particular an annular peripheral zone, wherein the peripheral zone suitably adjoins the edge of the bell cup and may have a width of, for example, between 0.05 mm and 10 mm (preferably 2 mm+/−1 mm), and wherein preferably only the peripheral zone is provided with a surface structure, wherein the remaining part of the inner face or at least a large part thereof may preferably be designed without a surface structure.

In the context of the invention, the hollow drive shaft may, for example, enclose a hollow inner pipe, whereby the disinfectant can be supplied to the bell cup via the hollow inner pipe.

The base of the bell cup is preferably used for mounting to allow the bell cup to rotate with the hollow drive shaft.

The inner face is used in particular to distribute and/or convey the disinfectant to the bell cup spray edge.

The passage through the hollow drive shaft can have a cross-section of, for example, between 3 mm and 30 mm.

FIG. 1 shows a schematic view of an apparatus 100 according to an embodiment of the disclosure for disinfecting at least one room, in particular a dwelling space for one or more persons. The dwelling space may be, for example, a human or veterinary treatment room, in particular a sickroom, a patient room and/or an operating theatre, for example in a hospital or doctor's surgery.

The apparatus 100 includes an atomiser for a disinfectant to disinfect the dwelling space and is characterised, for example, by the fact that the atomiser includes a rotatable bell cup 1 for atomising the disinfectant into the dwelling space.

An electric motor 2 or an air turbine is provided to drive the bell cup 1 and thus cause it to rotate by means of a hollow drive shaft S, which also advantageously serves to feed disinfectant to the bell cup 1. A supply line is provided in the hollow drive shaft S for this purpose. The bell cup 1 is suitably permanently attached to the drive shaft S.

The bell cup 1 works in conjunction with a disc-shaped cup P, which co-rotates with the bell cup 1. The bell cup 1, the drive shaft S and the cup P are essentially arranged coaxially with one another.

The disinfectant emerging from a disinfectant outlet nozzle D of the drive shaft S meets the rotating cup P and is thereby distributed through centrifugal force onto an inner face 1a of the rotating bell cup 1 (FIG. 9), from where the disinfectant is led to an annular bell cup spray edge E, from where it is atomised and sprayed into the dwelling space.

In operation, the bell cup 1 has a speed of preferably at least 30,000 revolutions per minute and an atomising capacity of at least 50 millilitres per minute and/or at least 0.3 cubic metres per minute.

Bell cups and their mode of operation, in particular with a co-rotating cup, are common in the technical field of painting motor vehicle bodies by means of rotary atomisers, so that these may be referred to for details. At this the bell cup serves to atomise the paint and to discharge it onto the vehicle body in the form of a paint spray jet in order to produce a paint path.

A first blower 3 is suitably disposed upstream of the bell cup 1, with a second blower 21, preferably designed as a side blower, disposed downstream of the bell cup 1. The blowers 3, 21 serve to convey and distribute disinfectant atomised by means of the bell cup 1, so that atomised disinfectant can be optimally distributed in the dwelling space. This ensures that the disinfectant reaches, insofar as possible, all surfaces to be disinfected (e.g. walls, ceilings, furnishings, surfaces facing away, etc.) in order to disinfect them. Blowers 3 and 21 can, for example, have a total air capacity of over 200 or even over 300 cubic metres per hour.

The bell cup 1, the electric motor 2 or the air turbine and blower 3 are housed at least partially in an atomiser housing Z.

A disinfectant line L1 comprising the drive shaft S connects the bell cup 1 with a connecting device V. The connecting device V is used to connect to a container 4 for holding the disinfectant. The disinfectant line L1 thus serves in particular to supply disinfectant to the bell cup 1. A delivery device 10, for example a pump, is then used to convey and dose the disinfectant.

The apparatus 100 includes two flow measuring devices 11a, 11b for measuring a volume flow, in particular of the disinfectant. A first flow measuring device 11a is disposed between the bell cup 1 and a bell cup valve 9 disposed downstream of the delivery device 10. A second flow measuring device 11b is disposed between the delivery device 10 and the bell cup valve 9 arranged downstream of the delivery device 10.

At least one air dehumidifier 14 is used to dehumidify air in the dwelling space, in particular after atomisation of the disinfectant has ended. The dehumidifier(s) 14 preferably have a total dehumidification capacity of over 600 or over 700 cubic metres per hour.

A receiving container 13, for example in the form of a trough, serves for the collection and recovery of liquid lost during the disinfection process.

The receiving container 13 is connected with the atomiser housing Z via a funnel 12 in order to receive liquid which is deposited on or in the atomiser housing Z, in particular from the disinfectant.

The receiving container 13 is also connected to the dehumidifier 14 in order to receive liquid that the dehumidifier 14 extracts from the room air.

The receiving container 13 is also connected to the delivery device 10 via a line L3, so that liquid can be led to the receiving container 13 when there is excess pressure at a relief valve 18 disposed in line L3. Alternatively, the relief valve 18 can also be disposed in the disinfectant line L1, for example between the delivery device 10 and the bell cup 1, in particular on or adjacent to the second flow measuring device 11b, or on or in the delivery device 10.

The apparatus 100 includes a lost-liquid line L2, whereby the receiving container 13 can be emptied via the lost-liquid line L2 and can preferably be connected to the connecting device V, so that lost liquid can be led from the receiving container 13 via the connecting device V for example to the disinfectant container 4, which was previously emptied in the disinfection process, or to another container for disposal.

On its way from the receiving container 13 to the connecting device V, the lost liquid passes the following: a filter device 16 for filtering the lost liquid, the delivery device 10, a receiving container valve 7 disposed downstream of the filter device 16 and upstream of the delivery device 10, a lost-liquid return valve 8, disposed downstream of the delivery device 10 and upstream of the connecting device V, and the flow measuring device 11b.

A rinsing agent connection A serves to connect to a rinsing agent container 15 for receiving a rinsing agent in order to rinse, while in a rinsing mode, at least sections of the disinfectant line L1 and/or the lost-liquid line L2.

The rinsing agent connection A can be connected to the disinfectant line L1 via a rinsing agent line L4, the rinsing agent line L4 including a rinsing agent valve 6 before leading into the disinfectant line L1.

The apparatus 100 is thus not only operable in a disinfection mode, but is also operable in a recovery mode for recovering lost liquid resulting from the disinfection process and in a rinsing mode for rinsing at least sections of the disinfectant line L1 and preferably the lost-liquid line L2.

The delivery device 10 can be used universally. Thus, in disinfection mode, the delivery device 10 serves to convey disinfectant from the disinfectant container 4, in recovery mode to convey lost liquid from the receiving container 13, and in rinsing mode to convey rinsing agent from the rinsing agent container 15.

The lost-liquid line L2 connects to the disinfectant line L1 at two junction points P1 and P2.

Junction point P1 is disposed between the delivery device 10 and the bell cup valve 9 disposed in the disinfectant line L1 downstream of the delivery device 10.

Junction point P2 is disposed between the delivery device 10 and a disinfectant valve 5 disposed in the disinfectant line L1 upstream of the delivery device 10.

The rinsing agent line L4 connects to the disinfectant line L1 at a junction point P3, the junction point P3 being disposed between the delivery device 10 and the disinfectant valve 5 disposed in the disinfectant line L1 upstream of the delivery device 10.

The disinfectant passes the following during the disinfection process: the disinfectant valve 5 upstream of the delivery device 10, the bell cup valve 9 downstream of the delivery device 10, the delivery device 10, the electric motor 2 or air turbine, the hollow drive shaft S with the disinfectant outlet nozzle D and the two flow measuring devices 11a, 11b, the cup P and the bell cup 1.

The rinsing agent passes the following in rinsing mode: the delivery device 10, a section of the disinfectant line L1, the hollow drive shaft S with disinfectant outlet nozzle D, a section of the lost-liquid line L2, the flow measuring devices 11a, 11b, the bell cup valve 9 disposed in the disinfectant line L1 downstream of the delivery device 10, the electric motor 2 or air turbine, the bell cup 1, the cup P, the lost-liquid return valve 8 disposed in the lost-liquid line L2 downstream of the delivery device 10 and the connecting device V.

A humidity measuring device 19, for example with a regulating effect on the disinfection process of the apparatus 100, is provided, with the humidity measuring device 19 serving to measure humidity in the dwelling space. Thus, for example, the disinfection process can be stopped if no increase in humidity is detected in the dwelling space during the atomisation process.

A temperature measuring device 20 for example with regulating effect on the disinfection process of the apparatus 100, is provided, with the temperature measuring device 20 serving to measure temperature in the dwelling space.

A level measuring device 17a serves to measure a fill level in the receiving container 13, with a level measuring device 17b serving to measure a fill level in the rinsing agent container 15. A level measuring device can also be used, for example, to measure a fill level in the disinfectant container 4.

A space measuring device (not shown) is used to measure the dwelling space, the disinfection process being carried out by the apparatus 100 depending on the measurement data from the space measuring device (for example, adjustment of the dosing quantity of the disinfectant, the volume flow of the at least one fan 3, 21 and/or the process time, etc.), or the apparatus 100 being prevented from starting the disinfection process, for example if the space measuring device has determined that the apparatus 100 is wrongly positioned in the dwelling space or the dwelling space is unsuitable for disinfection by the apparatus 100.

The apparatus 100 may also include one or more detection devices (not shown) for detecting disinfectant, for detecting rinsing agent and/or for detecting a rotation speed of the bell cup 1. The apparatus 100 may be configured, for example, to interrupt or prevent its operation (for example to stop or not start at all) if the detection device detects an unsuitable disinfectant, an unsuitable rinsing agent and/or an unsuitable rotation speed of the bell cup 1.

Figure 2:
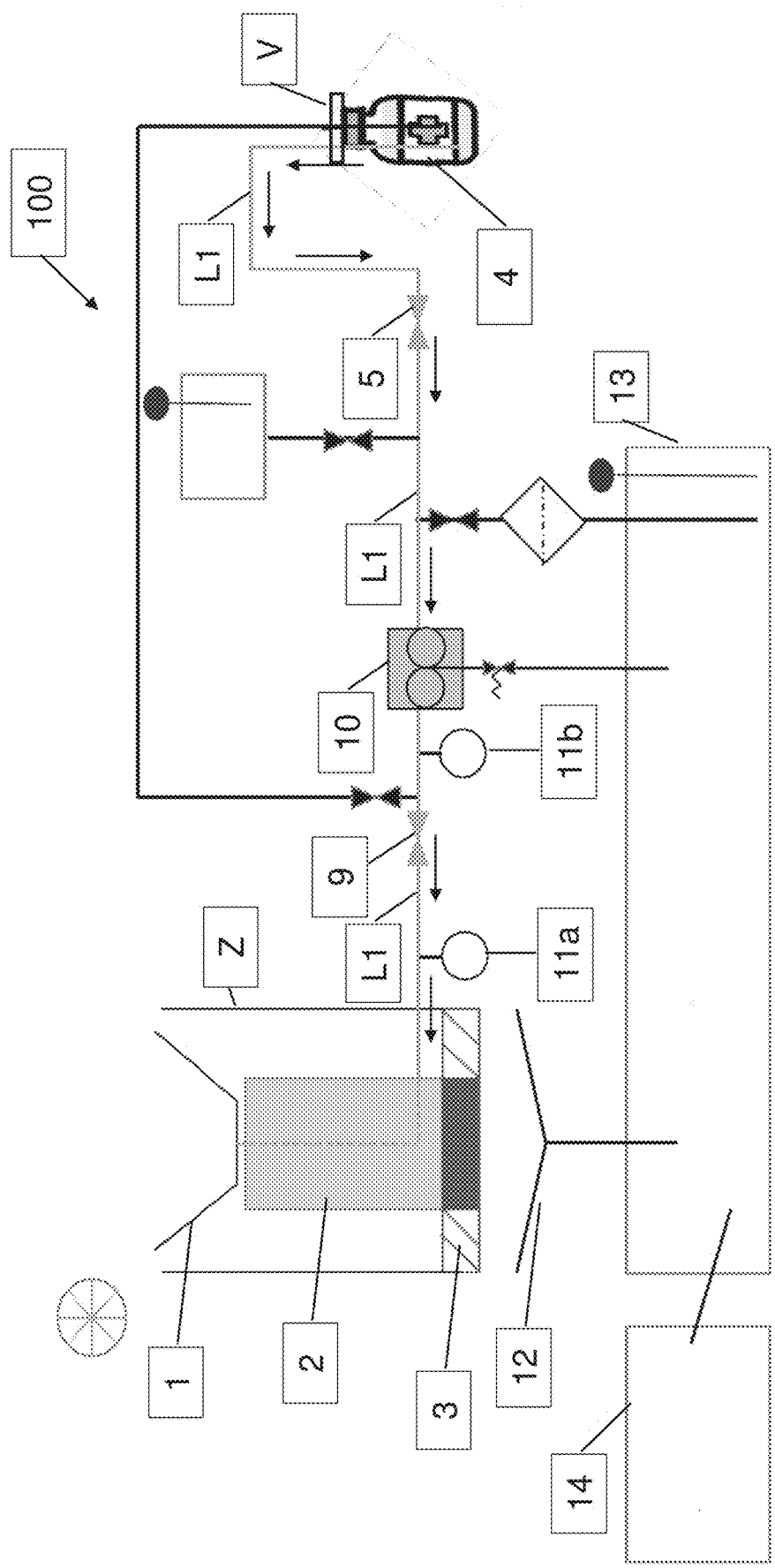
FIG. 2 shows a schematic view of the apparatus of FIG. 1, in particular to explain a disinfection process/mode, according to an embodiment of the, FIG. 3 shows a schematic view of the apparatus of FIG. 1, in particular to explain a lost-liquid recovery process/mode, according to an embodiment of the disclosure.
Figure 3:
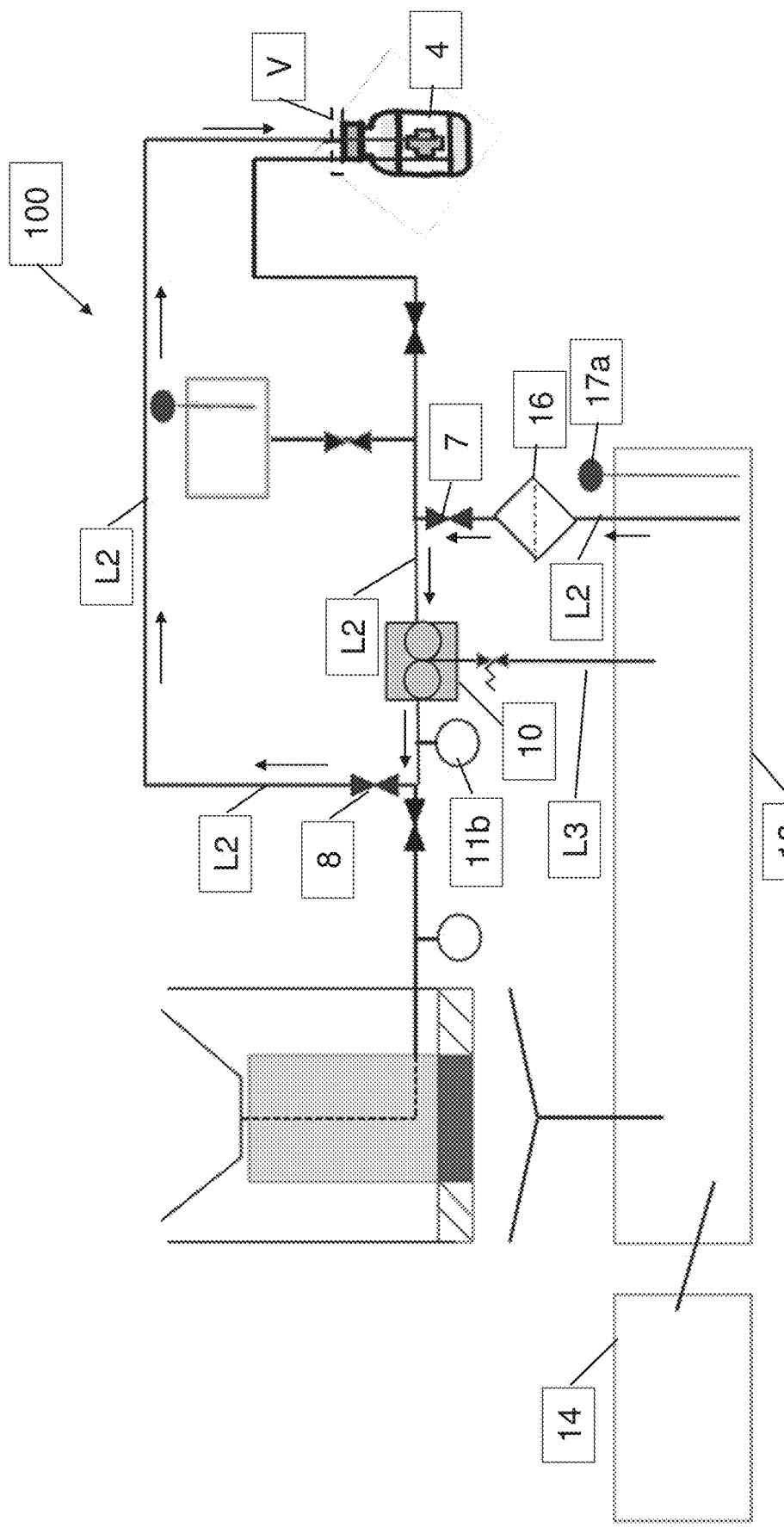
Figure 4:
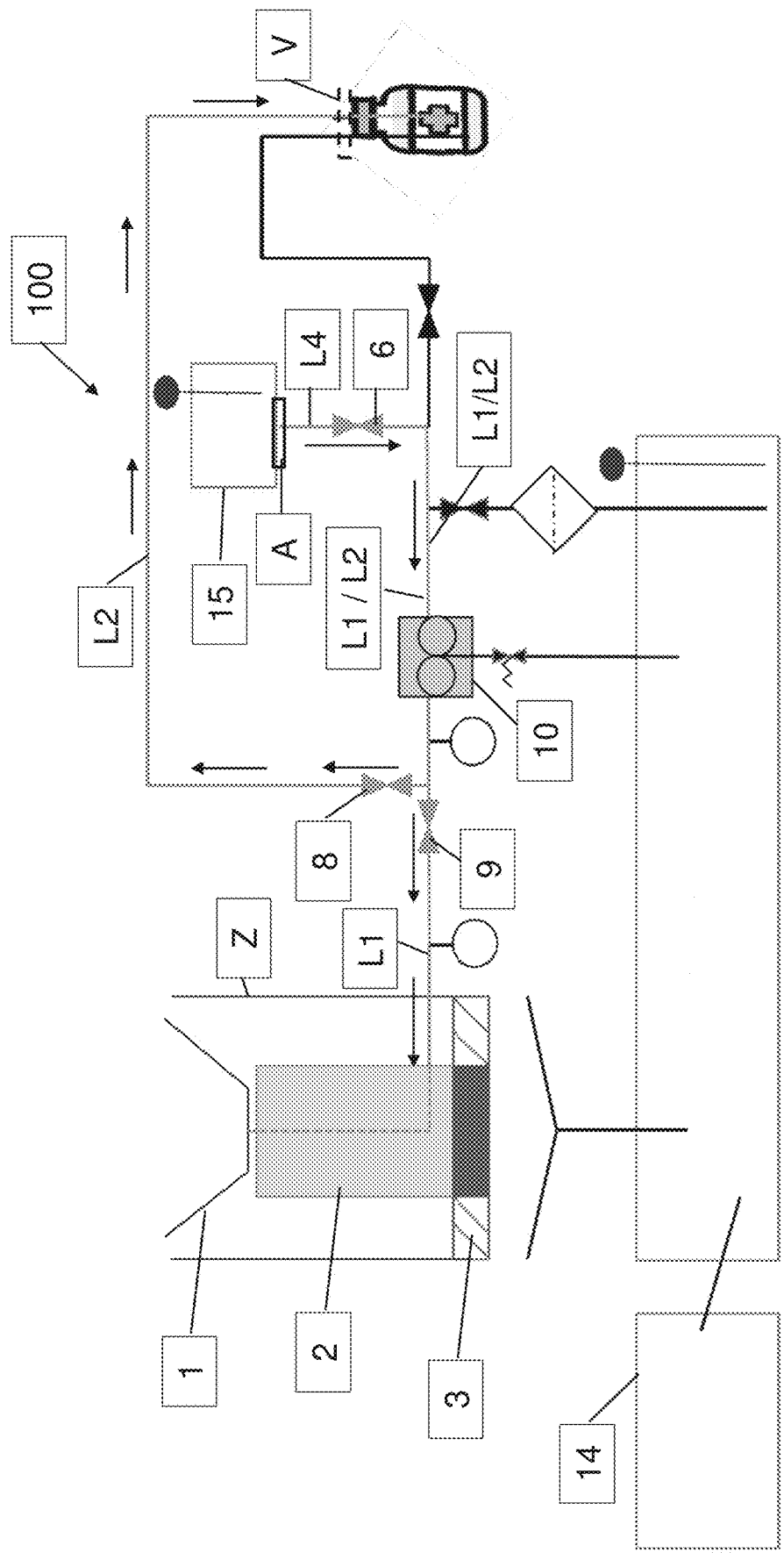
FIG. 4 shows a schematic view of the apparatus of FIG. 1, in particular to explain a rinsing process/mode, according to an embodiment of the disclosure.
Figure 5:
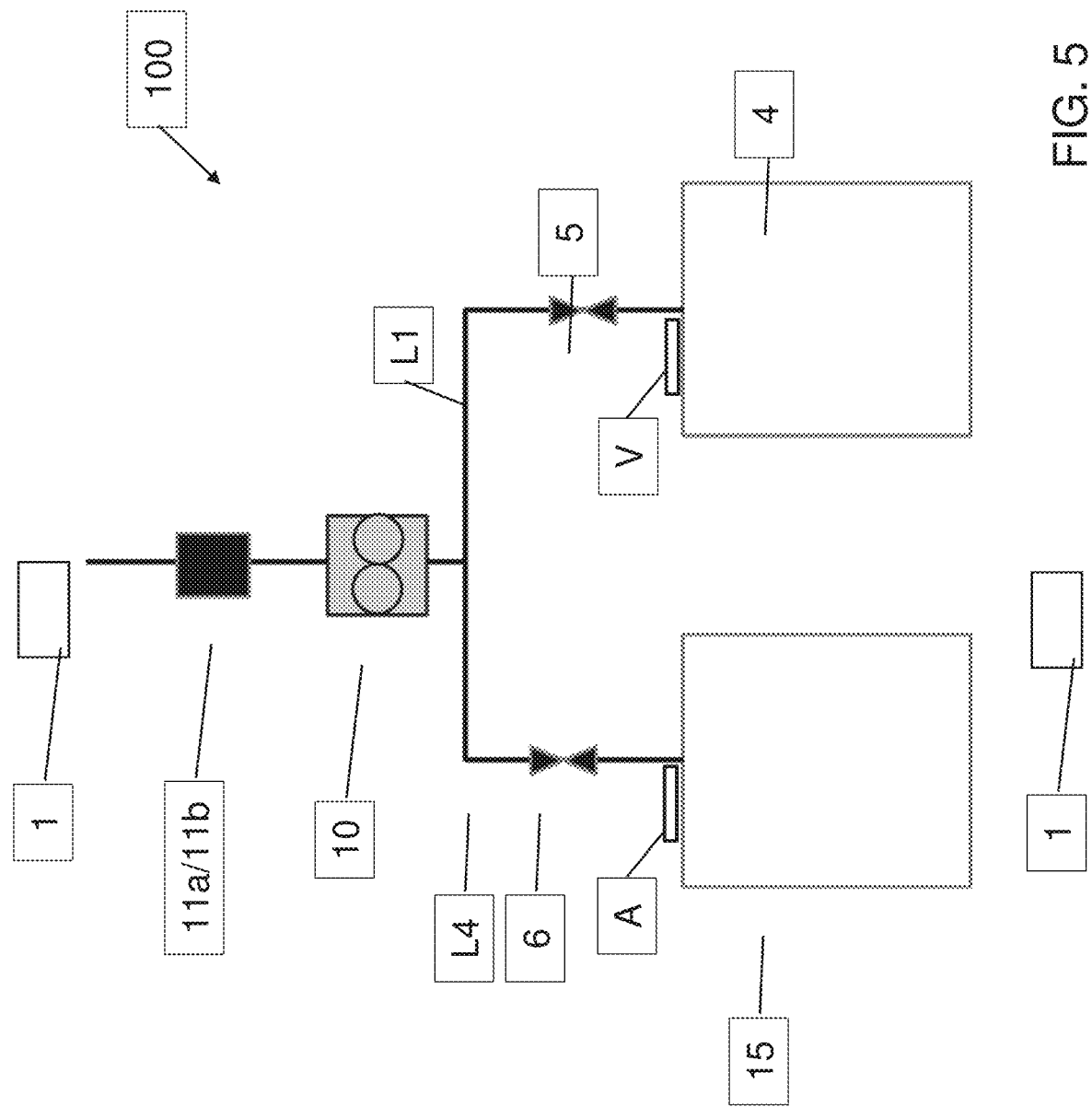
FIG. 5 shows a schematic view of a modified embodiment of the apparatus in FIG. 1 according to an embodiment of the disclosure.
Figure 6:
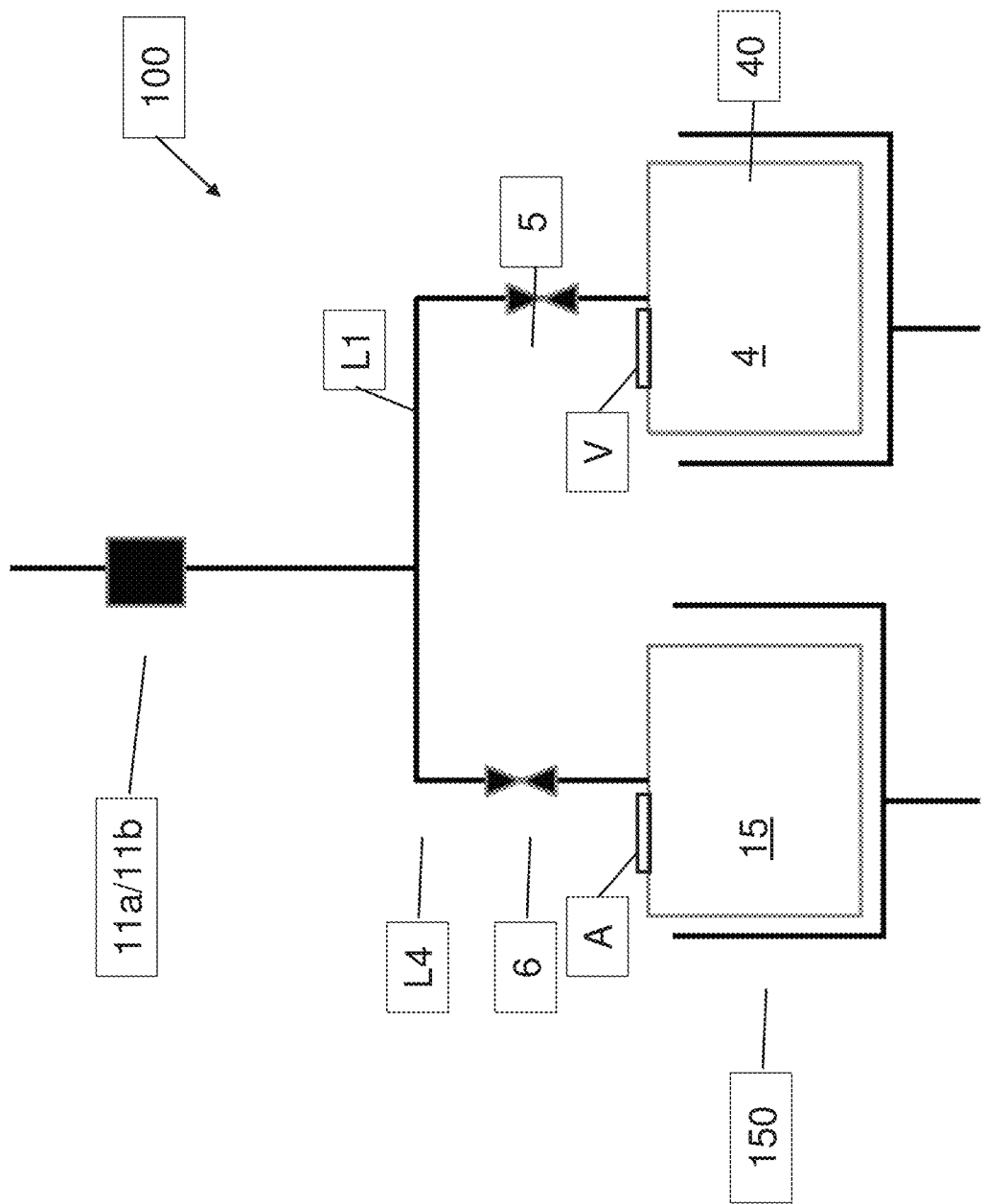
FIG. 6 shows a schematic view of a modified embodiment of the apparatus in FIG. 1 according to an embodiment of the disclosure.

FIG. 2 shows a schematic view of the apparatus 100, in particular to explain a disinfection process/mode according to an embodiment of the invention.

The disinfection process works essentially as follows:

The electric motor 2, the blower 3 and the temperature measuring device 20 are activated and operate based on process values for the disinfection process.

The disinfectant valve 5 and the bell cup valve 9 in the disinfectant line L1 are opened. The delivery device 10 is activated so that disinfectant is conveyed from the disinfectant container 4.

After a pre-defined period of x seconds, the flow measuring devices 11a and 11b record a volume flow of the disinfectant. If no or too small a volume flow is detected, the disinfection process is stopped immediately.

The blower 3 draws air from the environment and uses it to distribute atomised disinfectant in the dwelling space.

The pressure relief valve 18 protects the apparatus 100 from excess pressure.

The funnel 12 collects any moisture possibly deposited on or in the atomiser housing Z during the disinfection process and leads it to the receiving container 13.

After a pre-defined period (volume of disinfectant container 4/volume flow) and if the flow measuring device 11*a* does not detect any flow, the disinfection process is ended. The delivery device 10 then stops running. The disinfectant valve 5 and the bell cup valve 9 in the disinfectant line L1 are closed. The electric motor 2 is switched off. The blower 3 changes its mode of operation suitably and is used, for example, for a dwell time process based on process values and/or for cooling the electric motor 2.

Due to the disinfection process, a relative humidity of, for example, between 85% and 99% may be generated in the dwelling space.

FIG. 3 shows a schematic view of the apparatus 100, in particular to explain a lost-liquid recovery process/mode, according to an embodiment of the invention.

The lost-liquid recovery process works essentially as follows:

The lost-liquid recovery process starts a predefined period of time before the air dehumidifier 14 completes the ventilation process.

Deposited liquid from the atomiser housing Z, water from the air dehumidifier 14 and possibly any liquid from the line L3 (only in case of excess pressure in the line system of the apparatus 100) are led to the receiving container 13 as lost liquid.

The receiving container valve 7 and the lost-liquid return valve 8 in the lost-liquid line L2 are opened. The delivery device 10 starts to convey the lost liquid from the receiving container 13 to the previously emptied disinfectant container 4 or to another container.

The filter device 16 prevents solid particles or generally unwanted parts from entering the pipe system of the apparatus 100.

When the flow measuring device 11*b* detects that no flow of lost liquid is present, the lost liquid recovery process is ended. It should be noted that the lost liquid recovery process is preferably ended within the time required for dehumidification of the dwelling space by the air dehumidifier 14.

The delivery device 10 stops running. The receiving container valve 7 and the lost-liquid return valve 8 in the lost-liquid line L2 are closed.

A small quantity of lost liquid may remain in the receiving container 13.

The level measuring device 17*a* checks whether the receiving container 13 is filled to a proper level. From this, it may be concluded whether or not the lost liquid recovery process was carried out properly.

FIG. 4 shows a schematic view of the apparatus 100, in particular to explain a rinsing process/mode according to an embodiment of the invention.

The rinsing process works essentially as follows:

The rinsing process starts after dehumidification by the air dehumidifier 14 has ended.

The electric motor 2 and the blower 3 start and operate based on process values for the rinsing process.

The rinsing agent valve 6, the lost-liquid return valve 8 and the bell cup valve 9 are opened. The delivery device 10 starts to convey rinsing agent from the rinsing agent tank 15.

The rinsing agent is conveyed partly to the bell cup 1 and partly back to the disinfectant container 4 or to another container.

The rinsing agent process is terminated after a predefined volume flow, for example after the delivery device 10 has been running for a predefined period. The delivery device 10 stops running. The rinsing agent valve 6, the lost-liquid return valve 8 and the bell cup valve 9 are closed. The electric motor 2 and the blower 3 stop running.

A small quantity of rinsing agent may remain in the pipe system.

FIG. 5 shows a schematic view of a modified embodiment of the apparatus 100 according to an embodiment of the invention.

A special feature of the embodiment shown in FIG. 5 is that a permanently fixed rinsing agent container 15 in the form of a refillable tank is attached to the rinsing agent connection A and a permanently fixed disinfectant container 4 in the form of a refillable tank is attached to the connecting device V.

Thus, in the context of the invention, the connecting device V and the rinsing agent connection A can be suitably designed as detachable or non-detachable connections.

FIG. 6 shows a schematic view of a modified embodiment of the apparatus 100 according to an embodiment of the invention.

A special feature of the embodiment shown in FIG. 6 is that the delivery device has a piston system 40 for conveying disinfectant from the disinfectant container 4 and a piston system 150 for conveying rinsing agent from the rinsing agent container 15. Consequently, there are two delivery devices (piston systems) 40 and 150. In an especially preferred embodiment, the disinfectant container 4 is designed as a single-use container accommodated in the piston system and/or the rinsing agent container 15 is designed as a single-use container accommodated in the piston system 150.

Figure 7:
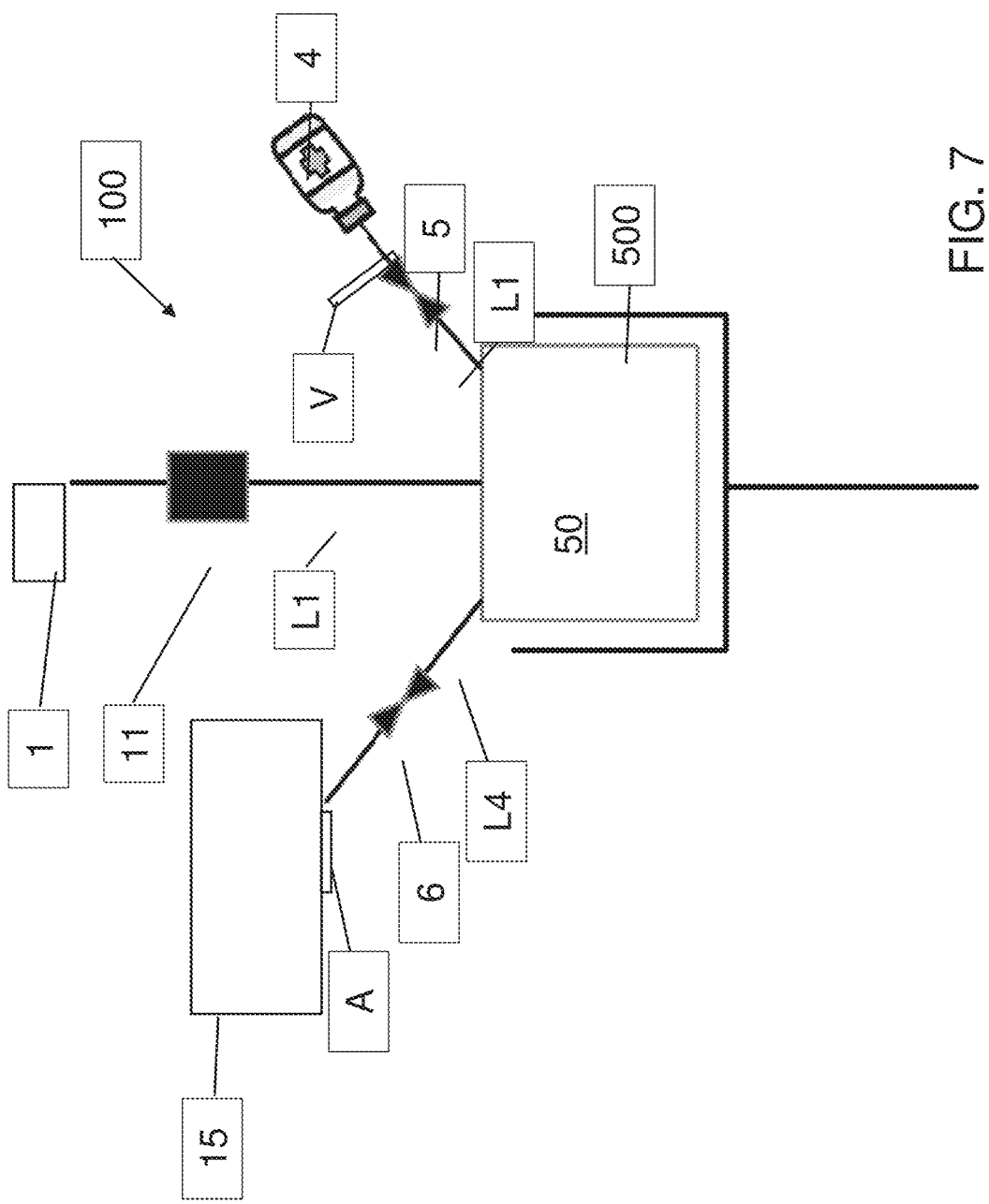
FIG. 7 shows a schematic view of a modified embodiment of the apparatus in FIG. 1 according to an embodiment of the disclosure.

FIG. 7 shows a schematic view of a modified embodiment of the apparatus 100 according to an embodiment of the invention.

A special feature of the design shown in FIG. 7 is that, instead of providing two separate containers 4 and 15 for disinfectant and rinsing agent, a multi-functional container 50 is provided to hold disinfectant for the disinfection process and also to hold rinsing agent for the rinsing mode, so that the multi-functional container 50 can be filled and operated first with disinfectant for the disinfection process and thereafter with the rinsing agent for the rinsing mode. The delivery device is designed as a piston system 500, with a multi-functional container integrated into the piston system 500. The multi-functional container 50 is integrated into the disinfectant line L1 and the rinsing agent line L4 and can be connected to the connection device V via the disinfectant valve 5 and to the rinsing agent connection A via the rinsing agent valve 6.

Figure 8:
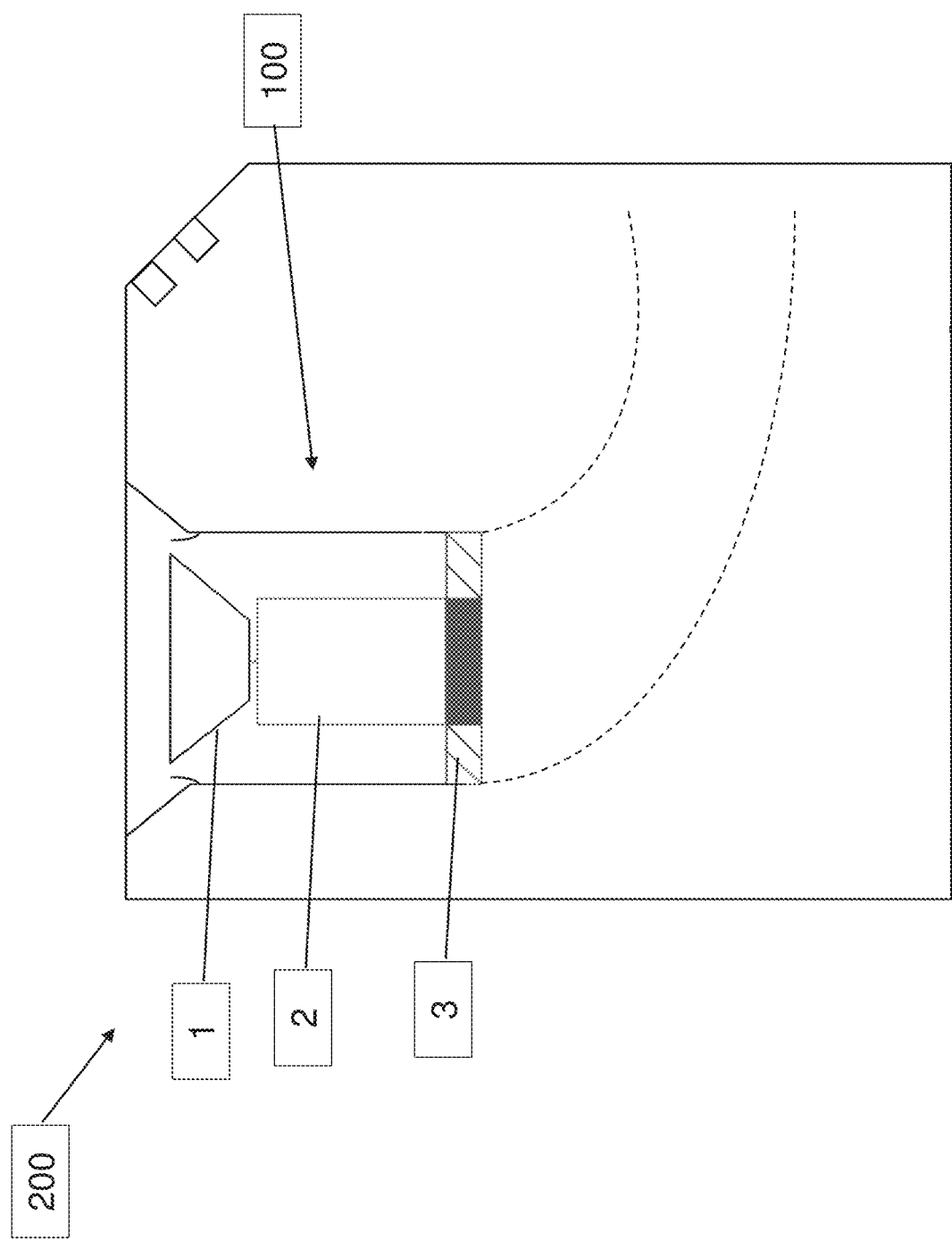
FIG. 8 shows a schematic view of a mobile transport housing according to an embodiment of the disclosure.

FIG. 8 shows a schematic view of a mobile transport housing 200 according to an embodiment of the disclosure with apparatus 100 housed inside.

The transport housing 200 with the apparatus 100 can be pushed into a dwelling space by an operator. The operator can then activate the apparatus 100 and leave the dwelling space. Once the disinfection process has ended, the operator can move the transport housing 200 with the apparatus 100 into another dwelling space to be disinfected. For this purpose, the transport housing 200 is part of a transport trolley fitted with rollers.

The transport housing 200 exposes the bell cup 1 at least partially in order to atomise disinfectant, the receiving container 13 being positioned below the level of the bell cup 1 and below the level of the blower 3, so that lost liquid can be led to the receiving container 13 by gravity. The transport housing 200 is provided with sound-absorbing material and includes a sealing cup to divide an inner space of the transport housing 200 into a dry section and a wet section.

Figure 9:
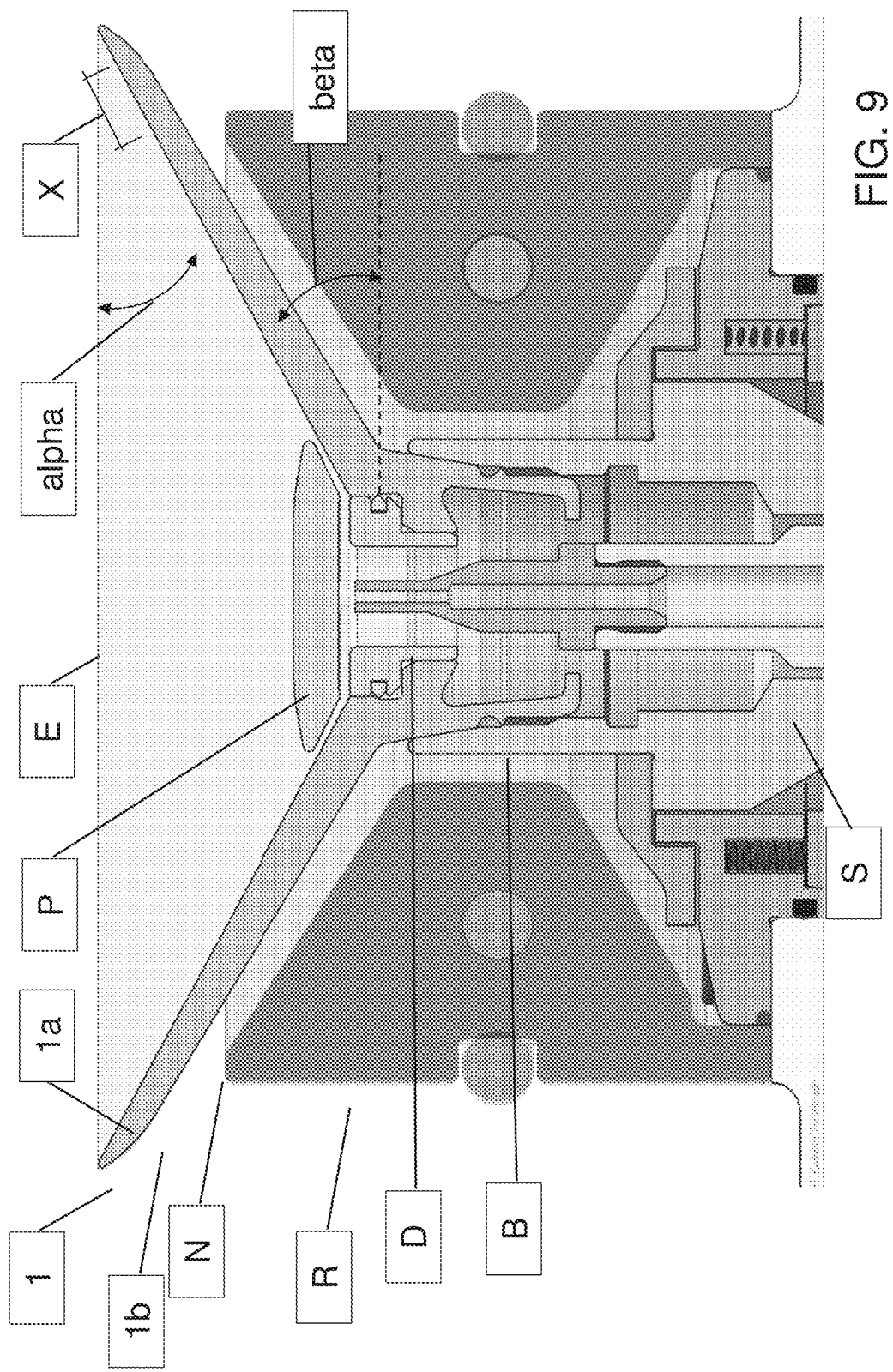
FIG. 9 shows a cross-sectional view of a bell cup and other components according to an embodiment of the disclosure.

FIG. 9 shows a cross-sectional view of a bell cup 1 and other components according to an embodiment of the invention.

The bell cup 1 is essentially funnel-shaped, with a base B (for example a mounting section), an inner face 1a for the disinfectant, an outer face 1b and an annular bell cup spray edge E. The bell cup 1 interacts with a cup P. Reference mark R indicates a gas directing ring with several leakage openings N. The gas is preferably air.

The inner face 1a can be formed straight, concave or convex.

The outer face 1b can be formed straight, concave or convex.

The base B is mounted so as to be rotationally fixed relative to the drive shaft S, so that the bell cup 1 can be driven by the drive shaft S. The cup P is mounted so as to be rotationally fixed on the bell cup 1 in order to rotate with the bell cup 1. The hollow drive shaft S encloses a hollow inner pipe through which disinfectant can be led to the bell cup 1, the disinfectant outlet nozzle D being suitably mounted on the inner pipe.

The annular bell cup spray edge E may, for example, have a diameter of between 65 mm and 120 mm, preferably 80 mm+/−10 mm, whereby an internal angle alpha of the inner face 1a of the bell cup 1 may be between 5° and 45°, preferably 30°+/−5°. An external angle beta of the outer face of the bell cup 1 can be between 1° and 80°. The internal angle alpha is preferably smaller than the external angle beta.

The inner face 1a of the bell cup 1 may have a peripheral zone, in particular an annular peripheral zone, the peripheral zone adjoining the bell cup spray edge E and having a width X of, for example, between 0.05 mm and 10 mm (preferably 2 mm+/−1 mm) and preferably only the peripheral zone being provided with a surface structure, but not the remaining part of the inner face 1a.

The passage for disinfectant through the hollow drive shaft S can have a cross-section of, for example, between 3 mm and 30 mm.

In the disinfection process of the apparatus 100, the disinfectant that emerges from the disinfectant outlet nozzle D meets the rotating cup P, is distributed by the rotating cup P onto the rotating inner face 1*a* and passes via the rotating inner face 1*a* to the rotating bell cup spray edge E, from where the disinfectant is atomised and discharged into the dwelling space.

The gas directing ring R with leakage openings N is disposed in such a way that gas discharged from the leakage openings N meets the disinfectant discharged from the bell cupl via the outer face 1*b* of the bell cup 1 in order to convert the disinfectant into the required form and/or reduce its droplet size.

The disinfection process is essentially as follows:

The disinfectant is led through the drive shaft S and sprayed out of the disinfectant outlet nozzle D of the drive shaft S, meets the cup P at a defined distance from the cup P and is directed by centrifugal force through a defined gap between the bell cup 1 and the cup P onto the inner face 1*a* of the bell cup 1*a*. The special geometry of the disinfectant outlet nozzle D and its defined distance from the cup P ensures that the disinfectant is led fully to the defined gap. This ensures a homogeneous distribution on the inner face 1*a*. Due to the centrifugal force caused by the rotation, the disinfectant is led along the specially adjusted inner faces 1*a* in the direction of the bell cup spray edge E. The disinfectant is atomised into very fine droplets at the bell cup spray edge E. The described process is improved, in particular the droplet size is reduced, as a result of the special geometry of the bell cup spray edge E and in combination with the shaping gas led from the gas directing ring R.

The guidance of the gas is improved due to the special geometry of the outer face 1*b* and the radius of the bell cup spray edge E. The shaping gas is preferably provided by a fan, runs upwards along the drive shaft S and flows around the outer face 1*b*. Due to the special geometry of the gas directing ring R, the forming gas is directed to the outer face 1*b* essentially without turbulence. The gas directing ring R also serves to reduce noise by preventing air vortex formation in the lower area of the outer face 1*b*, which area is covered by the gas directing ring R.

FIGS. 10 and 11 show two different perspective views of a bell cup 1 according to an embodiment of the invention. The bell cup 1 serves to atomise a disinfectant to disinfect at least one dwelling space for one or more persons and can be designed as disclosed herein.

It should also be noted that the disinfectant used with the disclosure can be, for example, the disinfectant disclosed in US 2014/0119992 A1 and/or other suitable disinfectants to eliminate, in particular, bacteria, viruses, germs and/or fungi, etc. The disinfectant is, in particular, a liquid disinfectant.

It should also be noted that the dwelling space can preferably be a room accessible by one or more persons.

The disclosure is not limited to the preferred embodiments described above. Rather, a large number of variants and modifications are possible, which also make use of the inventive step and thus fall within the scope of protection. Furthermore, the disclosure also claims protection for the subject matter and features of the dependent claims independently of the features and claims referred to. The disclosure may also include embodiments without a bell cup.

The invention claimed is:

1. A disinfection device comprising:
- an electric turbine having a distal end and a proximate end, the proximate end including a hollow shaft, the electric turbine configured to spin the hollow shaft between 30,000 and 70,000 rpm;
- a rotatable bell cup including a distributor, the bell cup being removably fastened to the hollow shaft;
- an internal supply line positioned in the hollow shaft;
- a disinfection line connected to the internal supply line and configured to deliver a disinfectant to the bell cup such that the bell cup atomizes the disinfectant;
- a blower located proximate the electric turbine at the distal end, the blower configured to distribute the disinfectant after it has been atomized by the bell cup;
- a pump configured to convey the disinfectant from a source of disinfectant to the bell cup via the disinfection line, wherein the source of disinfectant is upstream from the pump and the bell cup is downstream from the pump;
- a bell cup valve positioned between pump and the bell cup;
- a fluid line connecting the pump to a receiving container; and
- a valve positioned along the fluid line between the pump and the receiving container.

2. The disinfection device of claim 1 further comprising a funnel located between the blower and the receiving container.

3. The disinfection device of claim 1 further comprising an air dehumidifier configured to deliver moisture to the receiving container.

4. The disinfection device of claim 3 further comprising a rinsing agent connection that is in fluid communication with the disinfection line via a rinsing agent line that is connected to the disinfection line upstream from the pump.

5. The disinfection device of claim 4 further comprising a controllable rinsing agent valve positioned in the rinsing agent line.

6. The disinfection device of claim 1 further comprising a first flow measuring device positioned downstream from the bell cup valve.

7. The disinfection device of claim 6 further comprising a second flow measuring device positioned upstream from the bell cup valve.

8. The disinfection device of claim 7 further comprising a first lost liquid return line connected to the disinfectant line downstream from the second flow measuring device and upstream from the bell cup valve to return disinfectant back to the source of disinfectant.

9. The disinfection device of claim 8 further comprising:
- a second lost liquid return line connected to the disinfectant line upstream from the pump and configured to deliver disinfectant to the receiving container;
- a controllable receiving container valve positioned in the second lost liquid return line, and;
- a filter positioned in the second lost liquid return line.

10. The disinfection device of claim 1 further comprising an air directing ring proximate the bell cup and having an external angle beta that is larger than an internal angle alpha of the bell cup.

11. The disinfection device of claim 10 where the angle alpha is between and 35 degrees.

12. The disinfection device of claim 11 where the bell cup has a diameter of between 70 and 90 mm.

* * * * *

UNITED STATES PATENT AND TRADEMARK OFFICE
CERTIFICATE OF CORRECTION

| | |
|---|---|
| PATENT NO. | : 11,951,224 B2 |
| APPLICATION NO. | : 16/973797 |
| DATED | : April 9, 2024 |
| INVENTOR(S) | : Patrick Häussermann et al. |

It is certified that error appears in the above-identified patent and that said Letters Patent is hereby corrected as shown below:

In the Claims

Column 16, in Line 36, Claim 11, replace "is between and 35 degrees." with -- is between 25 and 35 degrees. --.

Signed and Sealed this
Fourteenth Day of May, 2024

Katherine Kelly Vidal
*Director of the United States Patent and Trademark Office*